United States Patent [19]

Halbert et al.

[11] 4,157,280

[45] Jun. 5, 1979

[54] TEST SET FOR DETECTING THE PRESENCE OF ANTIGENS ASSOCIATED WITH HEPATITIS

[75] Inventors: Seymour P. Halbert, Miami; Milton Anken, North Miami Beach, both of Fla.

[73] Assignee: Cordis Corporation, Miami, Fla.

[21] Appl. No.: 617,745

[22] Filed: Sep. 29, 1975

[51] Int. Cl.² ................... G01N 31/14; G01N 33/16
[52] U.S. Cl. .................. 195/127; 23/230 B; 424/12; 195/103.5 A
[58] Field of Search ................ 23/230 B, 253 R, 259; 195/103.5 R, 103.5 A, 127; 424/12

[56] References Cited

U.S. PATENT DOCUMENTS

| | | | |
|---|---|---|---|
| 3,646,346 | 2/1972 | Catt | 23/230 B X |
| 3,654,090 | 4/1972 | Schuurs et al. | 424/12 X |
| 3,700,609 | 10/1972 | Treagear | 260/2.5 R |
| 3,826,619 | 7/1974 | Bratu, Jr. et al. | 23/259 X |
| 3,876,504 | 4/1975 | Koffler | 23/230 B X |
| 4,016,043 | 4/1977 | Schuurs | 195/103.5 R |

OTHER PUBLICATIONS

Protapol DI/1, Imperial Chem. Ind., Melbourne, Australia, package flyer.
Catt et al., *J. Lab. and Clin. Med.*, vol. 70, pp. 820-822 (1967).
Belanger et al., *Clin. Chim. Acta*, vol. 48, pp. 15-17 (1973).
Ling et al., *Science*, vol. 180, pp. 203-205 (1973).
Engvall et al., *Biochim. Biophys. Acta*, vol. 251, pp. 427-434 (1971).
*Gradwohl's Clinical Laboratory Methods and Diagnosis*, vol. 1, pp. 355-357 (1970).

*Primary Examiner*—Sidney Marantz
*Attorney, Agent, or Firm*—Kenway & Jenney

[57] ABSTRACT

A test set useful for detecting the presence of antigens associated with hepatitis comprising an insoluble, polymeric disc-like solid having antibody reactive with antigens associated with hepatitis bonded thereto, an enzyme-hepatitis antibody conjugate reagent, an enzyme substrate solution, control sera negative, weakly positive, and strongly positive for antigens associated with hepatitis, an enzyme substrate buffer, and a horse globulin solution. Preferably, the enzyme of the conjugate is alkaline phosphatase, the enzyme substrate is p-nitrophenylphosphate and the substrate buffer has a pH on the order of 9.8.

13 Claims, 2 Drawing Figures

TEST SET FOR DETECTING THE PRESENCE OF ANTIGENS ASSOCIATED WITH HEPATITIS

BACKGROUND OF THE INVENTION

This invention relates to a test set useful in detecting hepatitis associated antigen in human body fluid.

Hepatitis B, formerly known as "serum hepatitis," is a disease which may be contracted by the parenteral or nonparenteral introduction of the hepatitis causative agent. Each year, in the United States alone, thousands of persons contract the disease after having received a transfusion of blood originating from a donor who has the causative agent in his blood. Since the disease has an incubation period lasting up to several months, a blood donor who as yet has not experienced any of the symptoms of hepatitis can unwittingly transmit the disease to an unsuspecting victim.

Those who contract hepatitis B invariably develop a hepatitis associated antigen in their blood streams. While, as yet, it is not known whether these antigens are themselves the causative agent of the disease, it is currently the best marker for the presence of that agent. Since the fairly recent discovery of a hepatitis associated antigen, a number of clinical detection procedures have been devised. These seek to provide a routine test, which can be performed on serum or plasma from blood samples and which is capable of screening blood containing the hepatitis associated antigen.

One such test is disclosed in U.S. copending application Ser. No. 617,743, entitled Method of Determining the Presence of an Antigen Associated with Hepatitis, by Seymour P. Halbert et al., filed on even date herewith, the disclosure of which is incorporated herein by reference. Briefly, the procedure involves incubating a small sample of fluid with an insoluble disc coated with purified antibodies reactive with antigens associated with hepatitis antigens. If hepatitis are present in the fluid, an immunochemical bond forms between the antigen and the immobilized hepatitis antibody. After washing away any soluble materials, the insoluble disc is subjected to a second incubation, this time with an enzyme tagged conjugate reagent. In the event antigen was present in the sample, a second immunochemical bond forms between the immobilized antigen on the disc and the enzyme tagged antibody. After another washing to remove any unbonded material, the disc is subjected to a third incubation with a substrate which, under the catalytic influence of the now immobilized enzyme, undergoes a chemical reaction to form a detectable end product. This end product can be present in the solution only if hepatitis antigens were present in the sample, since otherwise, no enzyme is immobilized, and the end product cannot be produced.

This procedure enables many samples, e.g., 100, to be tested simultaneously in about a 4 hour period. However, the success of the test, and particularly its sensitivity, is dependent, inter alia, on the concentrations and purity of the reagents used, the relative amounts of reagents used, and the degree of care employed by the technician during the procedure. Consequently, in order for the test to serve as a reliable and routine procedure for the detection of the hepatitis antigen, it is imperative that the reagents, reaction containers, etc., be supplied in a fashion designed to minimize human error, simplify the procedure, and standardize the steps involved so that accuracy and reproducibility may be easily maintained.

Accordingly, it is an object of the present invention to provide a unitized test set which is adapted for the performance of a sensitive, reproducible immunoassay of antigens associated with hepatitis on a routine basis by relatively unskilled persons.

Another object of the invention is to provide such a test set which is designed to minimize procedural errors in the performance of the immunoassay and which contains all the necessary reagents, reaction containers, etc. in a form designed to optimize the accuracy and sensitivity of the test.

Another object of the invention is to provide a test set containing laboratory equipment designed to standardize the various steps performed during the assay.

Still another object of the invention is to provide a test set containing standard control samples, negative, weakly positive, and strongly positive for hepatitis associated antigen, with which the test samples may be compared.

SUMMARY OF THE INVENTION

The three main reagents of the test set are an insoluble polymeric solid having antibodies reactive with antigens associated with hepatitis bonded thereto, enzyme tagged hepatitis antibody reagent, and an enzyme substrate capable of being chemically changed under the catalytic influence of the enzyme to form a detectable end product. In the preferred embodiment, the enzyme of the conjugate is an alkaline phosphatase and the enzyme substrate is p-nitrophenylphosphate. The test set also contains control sera including sera negative, weakly positive, and strongly positive for hepatitis antigens, a solution of a horse globulin additive for the test sample for minimizing the frequency of non-specific reactions between the test sample and the insoluble polymeric solid, a buffer designed to maintain the pH of the enzyme substrate solution in the optimum range for reaction, and a plurality of vials of a size calculated to promote contact between the insoluble solid and the small quantities of reagents used in the incubations. When alkaline phosphatase and p-nitrophenylphosphate are used as the enzyme-enzyme substrate system, the buffer is an aqueous solution 0.028 M in $Na_2CO_3$ and 0.001 M in $Mg^{++}$.

Other advantages and features of the invention will be in part pointed out and in part obvious from the following description of a preferred embodiment.

DESCRIPTION OF THE PREFERRED EMBODIMENT

Figure 1:
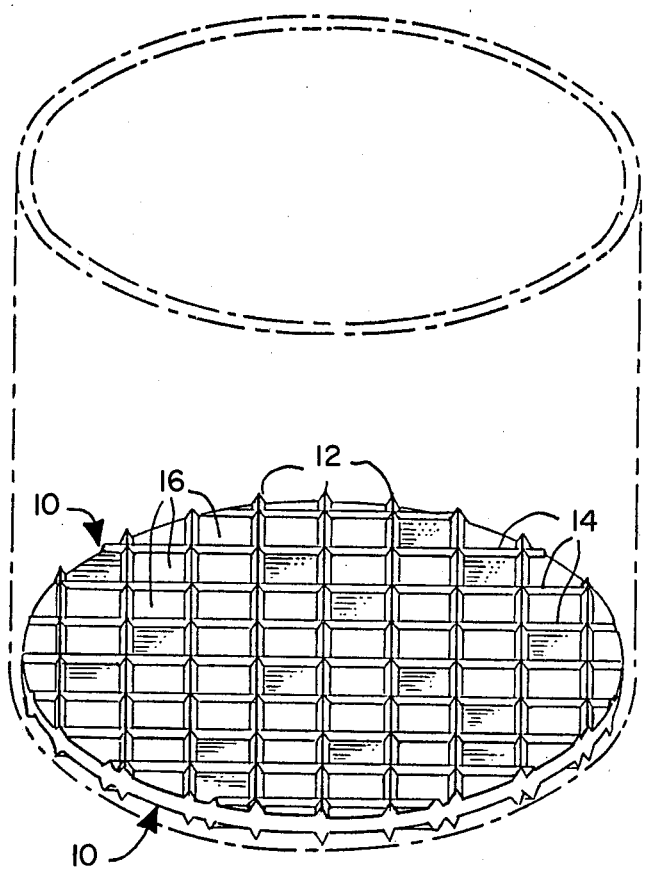
FIG. 1 is a perspective view of a disc (insoluble solid) comprising one element of the test set of the invention.

The hepatitis detection test set of the instant disclosure is designed for 100 tests. Obviously, larger or smaller sets may be manufactured by proportionally increasing or decreasing the quantities of reagents, etc. disclosed hereinafter. The kit is distributed in, e.g., a box, containing reagents and controls to be stored at 2°–8° C. until used. In addition, vials sufficient for conducting 100 tests are provided.

One hundred to one hundred and five polymeric discs, having waffle-like surfaces, as shown in the drawing, and having a layer of antibody reactive with hepatitis antigens bonded to their exterior and lyophilized are supplied. The exact nature of these insoluble solid discs and their method of manufacture are set forth below.

Preparation of Hepatitis Antibody

The preparation of hepatitis antibody depends first of all on obtaining blood which is known to be positive for antigens associated with hepatitis. Consequently, blood units obtained from various sources must first be evaluated to determine their suitability for preparing the immunospecific purified antibody of the invention.

A blood bag segment, containing blood which is believed to be positive for hepatitis antigens, is held at 2°–8° C. in an upright position to allow the blood cells to settle to the lower half. The plasma is separated from the cells and a titer is run on the undiluted plasma and a sample diluted 1:16 in normal saline against a standard antibody by the well-known technique of counterelectrophoresis (CEP). When both the undiluted plasma sample and the 1:16 diluted sample are positive, the blood unit is considered acceptable for use in the preparation of the purified antibody of the invention as described hereinafter.

Portion of antigens isolated from blood units are used for either stimulating antibody production in a host animal or purifying the antibody produced by that animal. The antigens must be subjected to a preliminary isolation process prior to either of the above uses.

The plasma is transferred to sterile vacuum container and clotted by adding a 5 M solution of a $CaCl_2$ on the basis of 0.75 ml $CaCl_2$ per 200 ml of plasma. This solution is then incubated at 37° C. in a water bath for one hour or until a clot forms. After a firm clot forms, the plasma is frozen at $-20°$ C. and allowed to thaw at 2°–8° C. to allow clot retraction. The serum is separated from the clot and filtered if necessary, then is ready for preparation of a hepatitis antigen pellet for immunization or for use in immunoabsorbent columns.

Preparation of Pellet for Immunization

Hepatitis positive sera which have been subjected to the above process are centrifuged at 10,000 rpm for 30 minutes at 4° C. The supernatant of this centrifugation is distributed into ultra centrifuge tubes and centrifuged in, for example, a Beckman L2-65B ultra-centrifuge, at 40,000 to 50,000 rpm for 4–20 hours at 4° C. The supernatant in each tube is removed and discarded; the pellet, which contains antigens, is given a preliminary rinse with normal (0.15 M) saline.

A small volume of normal saline is then added to each centrifuge tube and the contents are subjected to sonication to break up the pellet. The suspensions in the sonicator tubes are then pooled and redistributed equally into clean tubes which are filled with normal saline. This solution is again centrifuged in the Beckman L2-65B centrifuge at 40,000 to 50,000 rpm for 4–20 hours at 4° C., as mentioned above.

The procedure in the preceeding paragraph may be repeated 5 or more times.

The pellet material, after removing the supernatant from each centrifuge tube, is pooled in the minimal volume of normal saline. A sample is assayed against a standard hepatitis antibody. If the pellet titers at 1:25 or higher by CEP, it can be used for immunization. The pooled antigen pellet may be divided into 3 ml aliquots and frozen at $-20°$ C. for future use.

Production and Preliminary Purification of Hepatitis Antibody

A sample of the antigen pellet, prepared as described above, is added to an equal volume of FREUND'S complete adjuvant the morning of the immunization and an emulsion is prepared in accordance with procedures well known to those skilled in the art. The antigen is then injected into a host animal, e.g., a horse, in accordance with techniques known per se, to produce hepatitis antibody. The immunized horses are bled or subjected to plasmaphoresis according to conventional techniques. Alternatively, or in addition, preparation without adjuvant can be used with other routes of immunization.

These bleedings must be treated to isolate the hepatitis antibody in anticipation of the final immunoabsorption purification step. Broadly, this preliminary purification is accomplished in three steps. First, plasma from the host animal is recalcified. Second, the serum is mixed with a sufficient amount of normal human plasma (NHP) to precipitate antibodies other than those associated with hepatitis by inducing insoluble antigen-antibody complex formation. The absorbed antiserum is assayed for hepatitis antibody using CEP. Third, the antibody reactive with antigens associated with hepatitis is precipitated with ammonium sulfate. This material can be frozen until used.

Preparation of Charcoal Immunoabsorbent Column

The preparation of the purified antibody which is conjugated to produce the reagents of this invention is accomplished by subjecting the hepatitis antibody produced as disclosed above to an immunospecific extraction process. For a general discussion of this procedure, reference should be made to British Pat. No. 1,387,625 to Bradish et al., Mar. 19, 1975, entitled Immunospecific Separation of Antigens and Antibodies, the disclosure of which is incorporated herein by reference.

In general, this purification process as utilized in the present invention, takes advantage of the ability of antibodies reactive with hepatitis antigens to complex with these antigens to the exclusion of other extraneous antibodies and proteins which are inevitably present in the antibody sample extracted from the bleedings.

A column is prepared by packing prewashed, sorbent carbon into a glass or plastic tube by using conventional techniques. A pool of antigen is prepared from at least six individual serum specimens to obtain a diverse mixture of hepatitis antigens. The pool is then adjusted to a protein concentration of between 1 and 2 mg protein per ml solvent, based on UV absorption.

To attach the antigen onto the carbon, this diluted solution is introduced at a flow rate within the range of 300 to 1,000 ml per hour. Seventy five mg protein should be added per gram of charcoal in the column. The effluent from the column is collected in 500 ml aliquots, each of which are checked for protein content. The column is considered saturated with the antigen when the effluent has a protein content approximately equal to that of the starting material. The bed is washed by flowing phosphate buffered saline (PBS) through the column until the effluent shows no appreciable detectable absorption of 280 nm.

To elute any loosely attached protein, the charcoal bed is flushed with freshly prepared 5 M sodium iodide solution containing 200 mg per liter of sodium thiosulfate. Afterwards, the sodium iodide solution is flushed from the column by running a sufficient volume of PBS therethrough. After a final washing of the bed with PBS containing 1 mg per ml sodium azide (preservative), the column can be stored at 2°-8° C. until ready for use.

Preparation of Purified Antibody

The antibody, purified and described above, is freed of ammonium sulfate and diluted with PBS on the basis of 1 part antibody to 2 parts buffer. The column is set up and situated so that fractions can be collected. The antibody solution is added continuously to the column with a flow rate of about 200 ml/hour. Effluent is collected and tested for protein and hepatitis antibody content to determine when the column is saturated with antibody. After saturation is achieved, the column bed is washed with PBS to remove loosely absorbed protein.

At this point, antigens immobilized on the charcoal column have formed a bond with the antibodies reactive with them. Other extraneous proteins and antibodies, nonspecific to the absorbed antigens have passed through the column and have been separated from the antibody.

To break this antibody-antigen bond, and to elute the purified antibody, a 5 M solution of NaI prepared immediately prior to use is introduced into the column. The volume of NaI solution used should be sufficient to remove all antibody bound to the column. With the flow rate of the column set at least 200 ml per hour, the eluate is collected in fractions of appropriate volumes. The total amount collected should be at least equal to the volume of sodium iodide solution added.

As each fraction of the purified antibody is collected, it is subjected to a dual filtration; first, through a 0.45μ membrane, and second, through a 0.22μ membrane. The filtrate is diluted 1:3 using distilled water at 2°-8° C., e.g., 200 ml of filtrate is added to 400 ml of distilled water. These diluted antibody fractions are then added to, for example, an AMICON concentrator equipped with an XM-50 membrane, and the fractions are concentrated.

As a last purification step, the concentrated, purified, antibody is dialyzed. Following dialysis, the antibody is removed and centrifuged. The supernatent is dialyzed for at least 24 hours against 0.01 M sodium phosphate solution, as compared to against PBS in the first dialysis. After completion of this final dialysis, protein concentration of the antibody is measured.

The antibody is then assayed for activity against the standard antigen according to the CEP technique to determine antibody content and, if found acceptable, is lyophilized and stored until used.

The Antibody Coated Discs

U.S. Pat. No. 3,700,609 entitled Graft Copolymers, to G. W. Tregear et al., the disclosure of which is incorporated herein by reference, discloses an insoluble continuous polymeric substance comprising a polymeric backbone onto which side chains of another polymer or copolymer are grated. By suitable choice of the grafted polymer, it is possible to chemically link biological substances to the insoluble substrate. A product which is disclosed in the above patent is commercially available in a disc form under the tradename PROTAPOL DI/1 from Imperial Chemical Industries of Austrailia and New Zealand (ICIANZ).

The PROTAPOL DI/1 comprises a polytetrafluoroethylene backbone having isothiocyanopolystyrene groups grafted uniformly over its surface and is designed for use in radioimmunoassay. The discs, as presently available, are approximately 0.01 inches thick and 0.5 inches in diameter.

Figure 2:
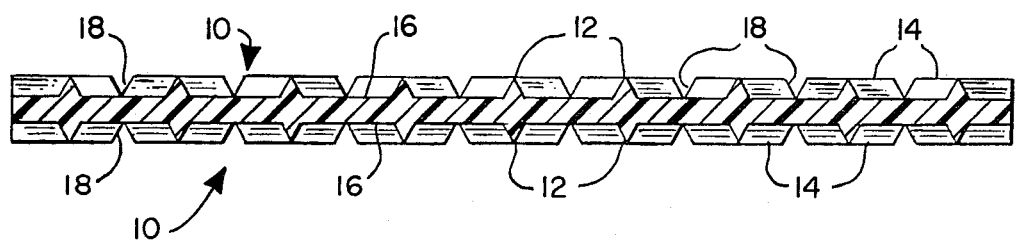
FIG. 2 is a cross-section view of the disc of FIG. 1 in the test set of the invention.

In accordance with one important embodiment of the present invention, each disc is provided with a wafflelike pair of surfaces 10 comprising a first series of linear ridges 12 and a second series of linear ridges 14 which form grids. Ridges 12 and 14 are preferably perpendicular to each other and hence define a plurality of square depressions 16. As seen in FIG. 2, the sides of each ridge 12 and 14 taper upwardly from adjacent pairs of depression 16 to form a line defining the top of the ridge. It should be noted that in order to facilitate the description of the invention, the ridges 12 and 14 are greatly exaggerated in the drawing.

The desired configuration of the disc is achieved by passing the disc through rollers having projections on the surface of the rollers designed to impart the desired configuration on the disc. As is obvious, the rollers are designed to provide a sufficient amount of pressure to disfigure the polymeric material in the disc without actually puncturing the disc. This fact is important because it should be noted that the disc has a reactive layer on its surface. Thus, penetration of the disc would expose the teflon to which no antibody can be bonded. Exposure of the teflon layer would actually result in a disc which would have a lower bonding capacity.

The main consideration is to provide a disc matrix with surfaces which, when placed in a flat bottomed vial, will be substantially in complete contact with the test sample, i.e., there should be a minimum of surface to surface contact between the matrix and the bottom of the vial. In another important embodiment of the invention, the disc is configured to have a field of high points and low points.

The hepatitis antibody which is to be attached to this insoluble solid is preferably prepared as disclosed above. This purified hepatitis antibody must be attached to the disc such that its immuno-reactive groups remain accessible, and its activity is not altered by the attachment process.

The antibody, which typically has been preserved in the lyophilized state, is reconstituted by adding 100 ml of 0.1 M NaHCO$_3$ (pH 9.6) for each 5.0 mg of antibody. In general, the procedure for attachment involves contacting 1000 waffled discs with the dilute solution at 2°-8° C. for 8 to 16 hours, with agitation. Afterwards, the antibody solution is discarded and the discs are washed twice with successive volumes of 0.1 M NaHCO$_3$, pH 9.6, phosphate buffered saline, and cold (2°-8° C.) 0.3% bovine serum albumin in phosphate buffered saline with 0.5% TWEEN 20. After an additional washing the crystalline bovine serum albumin, and freezing over dry ice, lyophilization is carried out and the discs are stored at 2°-8° C. until ready for use.

Although the description in this specification relates to the preparation of discs having hepatitis antibody bonded thereto, it should be apparent to those skilled in the art that the disc of the present invention is useful to immobilize an almost limitless number of proteins. For example, the increased contact between the test sample and the disc enables the disc to be used in tests which involve the bonding of the following proteins thereto: antibodies to drugs such as digoxin, opiates, steriods; antibodies to natural products, for example insulin and other hormones; and, specific enzymes to metabolites found in blood and other body fluids.

EXAMPLE

The following procedure was used to prepare 8,000 discs, each of which were first treated with the press to produce the desired configuration as described. A batch of 8,000 discs requires 40 mg of hepatitis antibody, i.e., 5 mg per 1,000 discs. The protein content of the reconstituted hepatitis antibody is adjusted to 0.05 mg/ml in a final volume of 800 ml in 0.1 M $NaHCO_3$ (pH=9.5). The entire 800 ml of buffered antibody is then added to a 1,000 ml screw-cap bottle provided with a leak proof liner containing the 8,000 discs, and the bottle is rotated for 16 hours, e.g., overnight, at 2°–8° C. to slowly tumble the discs through each rotation cycle. Afterwards, the liquid is poured from the bottle and discarded and the discs are transferred to a wide-mouth 2 liter flask.

The discs are washed twice with successive 1 liter volumes of cold (2°–8° C.) 0.1 M $NaHCO_3$ pH 9.6, following which the buffer is removed. The discs are then washed again, this time using two successive 1 liter volumes of cold buffer (0.01 M sodium phosphate, 0.15 M NaCl, pH=7.4). After removing residual buffer, the discs are washed for a third time, using two successive one liter volumes of cold bovine serum albumin solution (0.3%).

The discs are finally washed with two successive 1 liter volumes of a solution of cold crystalline bovine serum albumin (pH=8) at a concentration of 2 mg/ml. This step is performed to provide a protein environment for the protein on the disc. The discs, after removing the residual wash, are then transferred to dishes or trays (9"×9"), each of which is lined with a sheet of filter paper and each of which contains 200 ml of the crystalline bovine serum albumin solution. When the transfer is complete, a sheet of filter paper is used to cover them. Buffer is thoroughly removed. The discs are then quick frozen for 30 minutes on dry ice.

The contents of the tray are then lyophilized. The dry discs are then removed and stored in stoppered containers.

The second reagent in the set comprises a sample of hepatitis associated antibody-alkaline phosphatase conjugate. The exact nature of this reagent and the method for its preparation are disclosed in detail below.

Conjugating the Antibody with the Enzyme

Calf intentinal alkaline phosphatase is mixed with a solution of the reconstituted antibody in a ratio of 3:1, enzyme to antibody, to a final concentration greater than 10 mg of total protein per ml of solution in PBS (pH 7.4). The solution is dialyzed thoroughly to remove $NH_4^+$ ions.

The dialyzed antibody enzyme mixture is then centrifuged to remove any insoluble material. The protein content of the supernatant is adjusted to 10 mg/ml by adding the PBS-$Mg^{++}$ solution. To this solution 8% glutaraldehyde is added on the basis of 1 ml glutaraldehyde solution per 10 ml antibodyenzyme solution. After stirring slowly for 3.5 to 20 minutes, during which time the antibody and enzyme are chemically linked by the glutaraldehyde the solution of conjugate is dialyzed against PBS containing 0.001 M $Mg^{++}$ to remove the glutaraldehyde.

The dialyzed material is then centrifuged and the supernatant is diluted by addition of an aqueous solution of 0.05 M in tris (hydroxymethyl) aminomethane (pH 8) buffer, 1% normal human albumin (cystalline), 0.02% $NaN_3$, and 0.001 M in $MgCl_2$.

The conjugate is then diluted 8 fold with PBS, aseptically filtered, and dispensed into bottles in which it may be stored.

A third reagent supplied in the test set is 400 mg of p-nitrophenylphosphate enzyme substrate. This compound is stable in its powdered form, but, when dissolved in buffer to form a 1 mg/ml solution, becomes relatively unstable. Consequently, the solution must be prepared just prior to use.

The other components of the set will now be disclosed by outlining the general procedure employed for testing 100 blood units simultaneously, indicating what substances are supplied and how they are used. Two hundred or more glass, disposable, flat bottomed vials are supplied which have a diameter slightly greater than 0.5 inch, i.e., sized to match the 0.50 inch diameter of the discs. One hundred of these vials are used for the initial incubations and washings of the test, the other 100 are employed for the final incubation with the enzyme substrate.

To perform the assay according to the invention, 100 vials are set out in racks and each is identified to correspond to a test sample. To each vial is added 0.05 ml of the horse globulin solution, then 0.5 ml of sample is added to 95 of the vials. At this same time, three 0.5 ml samples of negative control serum are placed in each of three vials, a 0.5 ml sample of strong positive control serum is placed in one vial, and a 0.5 ml sample of weakly positive control serum is placed in another vial. As explained in detail in the aforementioned copending U.S. Pat. application Ser. No. 617,743, the controls are used for comparison with the test samples.

The negative control is made from human plasma which has been tested and found negative for hepatitis associated antigen by, for example, the technique known as radioimmunoassay (RIA). To each unit that is clearly negative for hepatitis antigen, 5M $CaCl_2$ is added to induce clotting, on the basis of 0.75 ml of $CaCl_2$ solution per 200 ml of plasma. This plasma is then incubated at 37° C. in a water bath until a clot forms. The clotted plasma units are then frozen at −20° C. and stored for at least 12 hours. The plasma units are then allowed to thaw at 2°–8° C. and the serum is collected. If the serum appears excessively turbid, it may be desirable to clarify it by centrifugation, e.g., at 9,000 rpm for 30 minutes at 2°–8° C.

Twenty grams of silica, e.g., AEROSIL-380, is added per liter of serum and mixed for 2 hours at room temperature to remove lipoproteins and stabilize the serum. The mixture is then centrifuged and the precipitate is discarded. If desired, the silica can be removed by filtration through appropriate filter media.

The supernatant is then further processed by filtration through, for example, MILLIPORE or HORM membranes and pads of successively decreasing porosity, the last being a 0.45 micron membrane. Before filtration through the 0.45 micron membrane, sodium azide ($NaN_3$) is added to the liquid in sufficient amount to provide a concentration of 0.1% by weight. As is well known in the art, sodium azide acts as a preservative. The final filtration, through a 0.45 micron or smaller porosity filter, should be done in a laminar flow environment using sterile equipment and techniques.

The sterile solution may be then stored at 2°–8° C. until ready for subdivision into reagent sized containers for use in the immunoassay. In the preferred, 100 test set, 7.5 ml of negative control serum are provided.

The positive control serum is produced from recalcified plasma from blood units which test positively for antigens associated with hepatitis. From each positive unit, a 1% sample is taken, and these are pooled together to form a trial pool. The trial pool is first heat treated for 10 hours at 60° C. to inactivate any hepatitis causative agent in the sample. When the pool has cooled to room temperature, a portion is removed and titrated against a standard antibody using the CEP technique to check that the antigen activity has been retained. To the trial pool is then added a sufficient amount of silica to provide a concentration of 20 g per liter of serum. The serum is then stirred using a stirring bar at room temperature for two hours after which it is centrifuged at 9,000 rpm for 30 minutes at 2°–8° C. The precipitate is discarded.

The supernatant is then titrated using CEP against a standard reference antibody. If the titer has remained at satisfactory levels, the total volume of all serum units may be pooled together and subjected to the same process as just described for the trial pool.

The trial pool and main pool are then combined and diluted with a sufficient amount of negative control serum to obtain optimum results with the positive control serum in the immunoassay of the invention. Preferably, the reading of the positive control serum in the test of the invention, in absorbance units × 1000, should be greater than 2000. This diluted positive control serum is then filtered through suitable media as before described, using a successive range of decreasing porosity. Before the final filtration through a 0.45 micron or smaller membrane, 0.1% by weight sodium azide is added. As with the negative pool, the final filtration should be done under aseptic conditions in a laminar flow environment.

The weakly positive control serum may be made by diluting the strong positive control with negative serum. The reading of the weakly positive serum as determined by the test of the invention should be between 600 and 1000. In the 100 test set of the preferred embodiment of the invention, 2.5 ml of strong positive control and 2.5 of weak positive control are supplied.

As indicated above, before one insoluble solid disc is added to each of the 100 vials, a 0.05 ml portion of horse globulin test sample diluent is added to each vial. This step is taken as a precaution to eliminate nonspecific reactions in the first incubation of the test samples with the insoluble discs. Although the antibody coated on the disc is purified and highly reactive with hepatitis antigens, there is occasionally present in human serum or plasma a substance capable of reacting with horse globulin per se that can thus form a bridge between the disc and the enzyme labeled conjugate, thus resulting in a false positive reaction. The horse globulin added in the first step binds this substance so it is not free to react with the disc. As disclosed above, the antibody coated on the disc is produced by immunizing a horse with hepatitis associated antigen collected from human blood. In the 100 test set of the invention, a 5.5 ml solution comprising 330 mg of horse globulin dissolved in phosphate buffered saline (PBS) is supplied.

To each vial containing the horse globulin and sample, including the control vials, is then added 1 antibody coated disc. The vials, with contents, are incubated for 0.5 hours at 43° C. in, e.g., a shaking water bath. During this incubation, hepatitis antigens present in the test sample or controls will combine with the antibody on the disc.

Prior to the addition of the enzyme-tagged antibody reagent to the vials containing the insoluble members, the supernatant from the first incubation must be removed and the insoluble members must be washed to remove any unbonded antigen. The wash solution is a 0.85% solution of sodium chloride, pH 6.5–7.5. After two 2.5 ml washes using this solution, 0.3 ml of the antibody-enzyme conjugate is added to each vial, and the vials are again incubated at 43° C. for 1 hour with shaking, during which time the enzyme tagged antibody will react with the hepatitis antigens that were fixed to the antibody coated disc during the first incubation.

As indicated above, the preferred conjugate comprises hepatitis antibody bonded to alkaline phosphatase. However, as pointed out in the aforementioned U.S. patent application Ser. No. 617,743, a very large number of enzymes may be substituted for the preferred one. Non-limiting examples of such enzymes include catalase, alcohol dehydrogenase, glycerol dehydrogenase, glyoxylate reductase, L-lactate dehydrogenase, malate dehydrogenase, glucose 6-phosphate dehydrogenase, mannitol 1-phosphate dehydrogenase, glucose oxidase, galactose oxidase, L-amino acid oxidase, D-amino acid oxidase, polyphenol oxidase, ascorbate oxidase, peroxidase, cholinesterase, phospholipase C, a-amylase, lysozyme, $\beta$-galactosidase, amyloglucosidase, $\beta$-glucuronidase, carboxypeptidase A. urease, aldolase, carbonic anhydrase, inorganic pyrophosphatase, and histidase.

After the second incubation, the supernatants are aspirated off and the discs in each vial are washed three times with 2.5 ml aliquots of the wash solution. This removes unreacted enzyme-antibody conjugate. Each insoluble member is then transferred to a clean vial and 2.5 ml of p-nitrophenylphosphate enzyme substrate-buffer solution is added to each vial (1 mg pNPP per ml). Since the optimum operational pH of the alkaline phosphatase-p nitrophenylphosphate system is 9.8, the enzyme substrate is dissolved in carbonate-$Mg^{++}$ buffer (pH=9.8±.1). This buffer as used comprises an aqueous solution 0.028 M in $Na_2CO_3$ and 0.001 M in $Mg^{++}$. Forty ml of concentrate is supplied with the set which, when diluted to 400 ml with distilled water, may be added directly to the 400 mg of pNPP. After addition of the buffered substrate, the vials are subjected to a third incubation for one hour at 43° C. with shaking. Different substrates must be employed if a different enzyme is used (see application Ser. No. 617,743).

Two drops (0.1 ml) of 3 M NaOH solution are then added to each vial to terminate the reaction. Each test set is supplied with 15 ml of 3 M sodium hydroxide for this purpose.

The enzyme substrate solution disclosed above changes from a colorless liquid to one having a yellow color in the event enzyme is present on the disc, i.e., in those vials containing samples positive for antigens associated with hepatitis.

The supernatant from the negative controls are pooled together in a suitable vial and their absorption is read at 405 nm in a spectophotometer against a distilled water blank. When the negative controls read less than 600 (absorbance units × 1000), they are considered as proper standards against which to compare the test results. Using the pooled negative control samples as a blank, test sample and positive control values are read, and the results are recorded as absorbance units × 1,000. With some spectrophotometers, it is possible to insert a negative control in the instrument, adjust the reading to zero, and read the value of the test samples directly. An unknown test sample whose optical density times 1,000 is greater than 100, using the pooled negative controls as a blank, is considered positive for antigens associated with hepatitis. This value has been selected to limit nonrepeatable positives which, if present, generally result from errors in laboratory technique.

The readings of the test samples may also be compared with the weak positive and strong positive control samples. Thus, not only the presence, but an indication of the concentration of hepatitis antigens in the sample may be obtained.

In view of the foregoing, it may be seen that the several objects of the present invention are achieved and other advantageous results have been attained.

The invention may be embodied in other specific forms without departing from the spirit of essential characteristics thereof. The present embodiment is therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. a test set useful for detecting the presence of antigens associated with hepatitis is a test sample comprising, in combination:

an insoluble polymeric solid having a layer of protein reactive groups grafted into its surface and having hepatitis associated antibody bonded to said reactive groups, the surfaces on said solid being distorted to comprise a field of high and low points to provide a solid which, when placed in a flat-bottomed vial, will be substantially in contact with any solution in the vial while minimizing surface-to-surface contact, said solid being for immobilizing hepatitis antigens from the sample;

an alkaline phosphatase - antibody conjugate reagent for labeling hepatitis antigen immobilized on said solid;

an enzyme substrate capable of being chemically changed under the catalytic influence of the alkaline phosphatase; and a flat-bottomed vial sized to receive said solid.

2. The set of claim 1 further including sera known to contain different concentrations of antigens associated with hepatitis.

3. The set of claim 2 wherein said sera include sera negative, weakly positive, and strongly positive for antigens associated with hepatitis.

4. The set of claim 3 further including a globulin solution for minimizing nonspecific immobilization of enzyme on said insoluble solid.

5. The set of claim 4 further including an alkaline phosphatase substrate buffer for optimizing the catalytic influence of the alkaline phosphatase on said substrate.

6. The set of claim 1 wherein said alkaline phosphatase enzyme substrate is p-nitrophenylphosphate.

7. The set of claim 6 further including an enzyme substrate buffer having a pH on the order of 9.8 for optimizing the catalytic influence of the alkaline phosphatase on the p-nitrophenylphosphate.

8. The set of claim 7 wherein said buffer comprises an aqueous solution 0.028 M in $Na_2CO_3$ and 0.001 M in $Mg^{++}$.

9. A test set useful for detecting the presence of antigens associated with hepatitis in a test sample comprising, in combination:

an insoluble polymeric sold having a layer of protein reactive groups grafted onto its surface and having antibodies to antigens associated with hepatitis bonded to said reactive groups, the surfaces on said solid being distorted to comprise a field of high and low points to provide a solid which, when placed in a flat-bottomed vial, will be substantially in contact with any solution in the vial while minimizing surface-to-surface contact, said solid being for immobilizing hepatitis antigens from the sample;

an alkaline phosphatase-hepatitis antibody conjugate reagent for labeling hepatitis antigens immobilized on said solid;

a quantity of p-nitrophenylphosphate for being exposed to the alkaline phosphatase to detect the presence thereof on said solid; and a flat-bottomed vial sized to receive said solid.

10. The set of claim 9 further including control sera negative, weakly positive, and strongly positive for antigens associated with hepatitis.

11. The set of claim 9 further including a horse globulin solution for minimizing nonspecific immobilization of antigen on said insoluble solid.

12. The set of claim 9 further including a buffer solution having a pH on the order of 9.8 for optimizing the catalytic influence of the alkaline phosphatase on the p-nitrophenylphosphate.

13. A test set useful for detecting the presence of antigens associated with hepatitis in a test sample comprising, in combination:

an insoluble polymeric solid having antibody reactive with antigens associated with hepatitis bonded thereto for immobilizing hepatitis antigens from the sample, the surfaces on said polymeric solid being distorted to comprise a field of high and low points to provide a solid which, when placed in a flat-bottomed vial, will be substantially in contact with any solution in the vial while minimizing surface-to-surface contact;

an alkaline phosphatase-hepatitis antibody conjugate reagent for labeling hepatitis antigens immobilized on said solid;

a quantity of p-nitrophenylphosphate for being exposed to the alkaline phosphatase to detect the presence thereof on said solid;

quantities of control sera negative, weakly positive, and strongly positive for antigens associated with hepatitis for comparison with the test sample;

an enzyme substrate buffer solution having a pH on the order of 9.8 for optimizing the catalytic effect of the alkaline phosphatase on the p-nitrophenylphosphate;

a horse globulin solution for minimizing nonspecific immobilization of enzyme on said soluble solid; and a flat-bottomed vial sized to receive said polymeric solid.

* * * * *